United States Patent [19]

Igari et al.

[11] Patent Number: 5,725,852
[45] Date of Patent: Mar. 10, 1998

[54] TRANSMUCOSAL THERAPEUTIC COMPOSITION

[75] Inventors: Yasutaka Igari, Kobe; Minoru Yamada, Kawanishi; Shigehisa Taketomi, Ikeda, all of Japan

[73] Assignee: Takeda Chemical Industries, Ld., Osaka, Japan

[21] Appl. No.: 526,987

[22] Filed: Sep. 12, 1995

Related U.S. Application Data

[62] Division of Ser. No. 049,402, Apr. 16, 1993, Pat. No. 5,482,706.

[30] Foreign Application Priority Data

Apr. 17, 1992 [JP] Japan ................... 4-097947

[51] Int. Cl.$^6$ .................... A61K 38/21; A61K 38/28; A61K 38/29
[52] U.S. Cl. .................... 424/85.7; 424/85.1; 424/85.2; 424/85.4; 514/3; 514/4; 514/12; 514/21
[58] Field of Search .................... 424/85.7, 85.1, 424/85.2, 85.4; 514/3, 4, 12, 21

[56] References Cited

U.S. PATENT DOCUMENTS

| | | | |
|---|---|---|---|
| 4,059,692 | 11/1977 | Takahashi et al. | 424/177 |
| 4,179,079 | 12/1979 | Hansen et al. | 514/4 |
| 4,386,077 | 5/1983 | Borgo | 424/180 |
| 4,572,832 | 2/1986 | Kigasawa et al. | 424/19 |
| 4,789,666 | 12/1988 | Gennari | 514/51 |
| 4,900,730 | 2/1990 | Miyauchi | 514/12 |
| 5,482,706 | 1/1996 | Igawi et al. | 424/85.7 |

FOREIGN PATENT DOCUMENTS

| | | |
|---|---|---|
| 0 214 898 | 3/1987 | European Pat. Off. |
| 0 477 885 | 4/1992 | European Pat. Off. |
| 2 666 987 | 3/1992 | France |
| 2 248 550 | 4/1992 | United Kingdom |
| WO/88/04556 | 6/1988 | WIPO |
| WO/88/09163 | 12/1988 | WIPO |
| 91/14454 | 10/1991 | WIPO |

OTHER PUBLICATIONS

Illum. Lisbeth, "The nasal delivery of peptides and proteins", TIBTECH, Vol. 9, Aug. 1991, pp. 284–289.

*Primary Examiner*—Chhaya D. Sayala

[57] ABSTRACT

A transmucosal therapeutic composition comprising a physiologically active peptide or protein and a cytidine nucleotide derivative was produced. The above composition results in a satisfactory transmucosal absorption of physiologically active peptides or proteins which are otherwise hardly absorbed from the mucosa. Since it allows self-administration to the mucosa, such as the nasal, vaginal or digestive tract mucosa, in lieu of injection which causes pain, the invention is of great utility as a pharmaceutical dosage form for physiologically active peptides or proteins which must be administered over a protracted time.

14 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: unknown
        ( D ) TOPOLOGY: linear     ( i i ) MOLECULE TYPE: peptide     ( i x ) FEATURE:
        ( A ) NAME/KEY: Peptide
        ( B ) LOCATION: 1
        ( D ) OTHER INFORMATION: /note="LOCATION 1, XAA =SER or AIB"

( i x ) FEATURE:
    ( A ) NAME/KEY: Peptide
    ( B ) LOCATION: 8
    ( D ) OTHER INFORMATION: /note="LOCATION 8, XAA =MET or a
        fat-soluble natural type amino acid"

( i x ) FEATURE:
    ( A ) NAME/KEY: Peptide
    ( B ) LOCATION: 11
    ( D ) OTHER INFORMATION: /label=peptide
        / note="Location 11, XAA =LEU, SER, LYS or an
        aromatic amino acid"

( i x ) FEATURE:
    ( A ) NAME/KEY: Peptide
    ( B ) LOCATION: 12
    ( D ) OTHER INFORMATION: /note="LOCATION 12, XAA =GLY or
        D-amino acid"

( i x ) FEATURE:
    ( A ) NAME/KEY: Peptide
    ( B ) LOCATION: 13
    ( D ) OTHER INFORMATION: /note="LOCATION 13, XAA =LYS or
        LEU"

( i x ) FEATURE:
    ( A ) NAME/KEY: Peptide
    ( B ) LOCATION: 18
    ( D ) OTHER INFORMATION: /note="LOCATION 18, XAA =Met or
        fat-soluble natural type amino acid"

( i x ) FEATURE:
    ( A ) NAME/KEY: Peptide
    ( B ) LOCATION: 19
    ( D ) OTHER INFORMATION: /note="LOCATION 19, XAA =Glu or a
        basic amino acid"

( i x ) FEATURE:
    ( A ) NAME/KEY: Peptide
    ( B ) LOCATION: 21
    ( D ) OTHER INFORMATION: /note="LOCATION 21, XAA =Glu or a
        basic amino acid"

( i x ) FEATURE:
    ( A ) NAME/KEY: Peptide
    ( B ) LOCATION: 23
    ( D ) OTHER INFORMATION: /note="LOCATION 23, XAA =Trp or
        2-(1,3- dithiolan-2-yl)Trp"

( i x ) FEATURE:
    ( A ) NAME/KEY: Peptide
    ( B ) LOCATION: 25
    ( D ) OTHER INFORMATION: /note="LOCATION 25, XAA =Arg or
        His"

( i x ) FEATURE:
    ( A ) NAME/KEY: Peptide
    ( B ) LOCATION: 26
    ( D ) OTHER INFORMATION: /note="LOCATION 26, XAA =Lys or
        His"

( i x ) FEATURE:
    ( A ) NAME/KEY: Peptide
    ( B ) LOCATION: 27
    ( D ) OTHER INFORMATION: /note="LOCATION 27, XAA =Lys, Gln
        or Leu"

( i x ) FEATURE:
    ( A ) NAME/KEY: Peptide
    ( B ) LOCATION: 34
    ( D ) OTHER INFORMATION: /note="LOCATION 34, XAA =Phe or
        Phe-NH2"

( x i ) SEQUENCE DESCRIPTION: SEQ ID NO:1:

```
Xaa  Val  Ser  Glu  Ile  Gln  Leu  Xaa  His  Asn  Xaa  Xaa  Xaa  His  Leu  Asn
 1                   5                        10                       15

Ser  Xaa  Xaa  Arg  Xaa  Glu  Xaa  Leu  Xaa  Xaa  Xaa  Leu  Gln  Asp  Val  His
```

2 0                    2 5                    3 0

Asn  Xaa ( 2 ) INFORMATION FOR SEQ ID NO:2:

( i ) SEQUENCE CHARACTERISTICS:
            ( A ) LENGTH: 34 amino acids
            ( B ) TYPE: amino acid
            ( C ) STRANDEDNESS: unknown
            ( D ) TOPOLOGY: linear ( i i ) MOLECULE TYPE: peptide ( i x ) FEATURE:
            ( A ) NAME/KEY: Peptide
            ( B ) LOCATION: 3
            ( D ) OTHER INFORMATION: /note="LOCATION 3, XAA =Ser or a
                    D-alpha- amino acid of 4 or less carbon atoms"

( i x ) FEATURE:
            ( A ) NAME/KEY: Peptide
            ( B ) LOCATION: 16
            ( D ) OTHER INFORMATION: /note="LOCATION 16, XAA =a
                    water- soluble alpha-amino acid"

( i x ) FEATURE:
            ( A ) NAME/KEY: Peptide
            ( B ) LOCATION: 25
            ( D ) OTHER INFORMATION: /note="LOCATION 25, XAA =a
                    water- soluble alpha-amino acid"

( i x ) FEATURE:
            ( A ) NAME/KEY: Peptide
            ( B ) LOCATION: 26
            ( D ) OTHER INFORMATION: /note="LOCATION 25, XAA =a
                    water- soluble alpha-amino acid"

( i x ) FEATURE:
            ( A ) NAME/KEY: Peptide
            ( B ) LOCATION: 27
            ( D ) OTHER INFORMATION: /note="LOCATION 27, XAA =a
                    water- soluble alpha-amino acid"

( i x ) FEATURE:
            ( A ) NAME/KEY: Peptide
            ( B ) LOCATION: 34
            ( D ) OTHER INFORMATION: /note="LOCATION 34, XAA =Phe or
                    Phe-NH2"

( x i ) SEQUENCE DESCRIPTION: SEQ ID NO:2:

Ser  Val  Xaa  Glu  Ile  Gln  Leu  Met  His  Asn  Leu  Gly  Lys  His  Leu  Xaa
 1              5                         10                          15

Ser  Met  Glu  Arg  Val  Glu  Trp  Leu  Xaa  Xaa  Xaa  Leu  Gln  Asp  Val  His
              20                         25                         30

Asn  Xaa

TRANSMUCOSAL THERAPEUTIC COMPOSITION

This is a divisional of application Ser. No. 08/049,402 filed on Apr. 16, 1993 now U.S. Pat. No. 5,482,706.

FIELD OF THE INVENTION

The present invention relates to a transmucosal drug delivery system for physiologically active peptides or proteins.

BACKGROUND OF THE INVENTION

It is by now well-documented that peptides such as hormones and cytokines are playing a diversity of critical roles in the body for the maintenance of life. Meanwhile, recent advances in synthetic technology and genetic engineering have enabled the industry to produce, in the pure form and in large quantities, such natural peptides or proteins and even their analogs having modified amino acid sequences and some of them are expected to be of use as medicines.

However, it is known that such physiologically active peptides or proteins generally are decomposed by digestive juices in the gastrointestinal canal or hydrolyzed by the enzymes on the digestive tract wall. It is also known that these substances are poorly absorbed after administration. Therefore, from the expectation to obtain sufficient pharmacological efficacy, these physiologically active peptides or proteins are commonly administered by parenteral injection instead of being administered orally. However, this route of administration is not only liable to cause pain in the patient but is burdensome to the patient because it does not provide for the choice of self-administration and these disadvantages are particularly remarkable when long-term repeated administration is required.

Recently, as an expedient method for administering such a physiologically active peptide or protein, a transmucosal drug delivery system insuring absorption of the peptide or the like from the nasal mucosa, digestive tract mucosa or vaginal mucosa has been proposed. According to this system, based on the rationale that a peptide or protein of high molecular weight, such as calcitonin, insulin or PTH, is hardly absorbed when administered alone, an absorption promoter is generally employed. As pharmaceutical preparations of this kind, the following are known.

Japanese Patent Application (hereinafter referred to briefly as JP) Laid Open No. 58-189118/1983 discloses a technology about a transnasal therapeutic preparation containing a physiologically active polypeptide and, as a transmucosal absorption promoter, a cyclodextrin compound.

JP [Laid Open] No. 59-89619/1984 and [Laid Open] No. 59-130820/1984 disclose the use of an amphoteric, ionic, e.g. cationic, or nonionic surfactant and teach that, among such surfactants, ether-form surfactants, such as polyoxyethylene lauryl ether, which are nonionic, are particularly high in the absorption promoting effect. However, ether-form surfactants implement the penetration of the drug only by impairing the nasal mucosa and because of this tissue-damaging potential, the clinical use of these surfactants cannot be straightforwardly recommended.

JP [Laid Open] No. 59-89619/1984, [Laid Open] No. 59-130820/1984, [Laid Open] No. 61-194034/1986, [Laid Open] No. 64-50823/1989, [Laid Open] No. 1-501550/1989 and [Laid Open] No. 2-503915/1990 disclose technologies about pharmaceutical compositions for administration into the nasal cavity which comprise some or other surfactant such as benzalkonium chloride, a bile acid salt or a phospholipid as an absorption promoter but since mucosal irritating effects are unavoidable, they can hardly be administered repeatedly for a long time.

JP [Laid Open] No. 61-118325/1986 discloses a calcitonin transnasal therapeutic composition containing a basic and/or neutral amino acid as the absorption promoter. JP [Laid Open] 61-126034/1986 discloses a similar composition containing aldose. JP [Laid Open] 61-267528/1986 discloses a composition containing polyethylene glycol 400, and JP [Laid Open] 63-39822/1988 discloses a composition containing a sucrose fatty acid ester. However, many of these absorption promoters are toxic to the mucosa.

JP [Laid Open] 1-501550/1989 discloses a transnasal therapeutic composition containing a polypeptide such as insulin and, as the absorption promoter, a phospholipid or a derivative thereof, such as a phosphatidylcholine, a phosphatidylethanolamine and so on. JP [Laid Open] 2-503915 discloses a technology employing a lysolecithin, lysophosphatidylethanolamine, lysophosphatidic acid or the like as a surfactant component. Although these substances are physiological substances and, as such, are metabolized in the body, they are surfactants of a sort and may have irritation potentials (Suzan, Chandler, et al., International Journal of Pharmaceutics, 76, pp. 61-70, 1991).

SUMMARY OF THE INVENTION

The object of the present invention is to provide a transmucosal therapeutic composition which comprises a physiologically active peptide or protein and a cytidine nucleotide derivative, which allows absorption of a physiologically active peptide or protein from the nasal, digestive tract, lung or vaginal mucosa with improved efficiency and without injuring the local mucosa.

DESCRIPTION OF THE PREFERRED EMBODIMENTS

The inventors of this invention discovered, after much research to solve the above-mentioned objects, that when a composition comprising a cytidine nucleotide derivative and a physiologically active peptide is administered intranasally or intravaginally, absorption of the peptide from the nasal or vaginal mucosa was remarkably enhanced. This finding was followed by further research which has brought the present invention into being. The subject matter of the present invention is, therefore, a transmucosal therapeutic composition comprising a physiologically active peptide or protein and a cytidine nucleotide derivative.

The physiologically active peptide or protein which can be used in the present invention includes but is not limited to antibiotics, hematopoietics, antiinfective agents, antidementia agents, antiviral agents, antitumoral agents, antipyretics, analgesics, antiinflammatory agents, antiulcer agents, antiallergic agents, antidepressants, psychotropic agents, cardiotonics, antiarrythmic agents, vasodilators, antihypertensive agents such as hypotensive diuretics, antidiabetic agents, anticoagulants, cholesterol lowering agents, therapeutic agents for osteoporosis, hormones, vaccines and so on.

The physiologically active peptide or protein which is employed in accordance with the present invention is a peptide composed of two or more amino acids and having physiological activity or a derivative thereof. Preferably, such a peptide has a molecular weight in the range of about 200 to 200000. The more preferred molecular weight range is about 200 to 100000 and the range of about 200 to 50000 is still more desirable.

This physiologically active peptide or protein can be a substance which is readily absorbed or a substance which is hardly absorbed when administered alone. The substance being hardly absorbed means a substance being not sufficiently absorbed in the absence of an absorption promoter, thus failing to provide a therapeutically effective concentration at the usual dosage level. Moreover, the mechanisms of action of such peptides are immaterial. Thus, they may be antagonists, agonists, their soluble receptors or derivatives thereof. Also included are muteins which are obtainable by partial substitution of, addition to, or partial deletion of the amino acid sequences of such peptides. Furthermore, fragments of these peptides or proteins are also included insofar as such fragments have the physiological properties of the parent peptides or proteins. With regard to peptides or proteins having carbohydrate chains, substances varied in the carbohydrate species are also included. In certain instances, such peptides or proteins may have been modified by a synthetic polymer, such as polyethylene glycol, or a natural polymer, such as hyaluronic acid, or even by an optional sugar (e.g. galactose, mannose), sugar chain or nonpeptide compound. The substances added in such modification may be those capable of binding to certain receptors or antibodies. The substances added in such modification may also be those capable of showing lipophilic properties such as phospholipid, fatty acid. Also included are hybrid peptides which are obtainable by addition of a peptide capable of binding to an optional receptor, antibody or the like to the amino acid sequence essential to the expression of the desired pharmacologic activity. Further included are peptides obtainable by chemical bonding of a plurality of peptides as well as those peptides which are expressed by the genes synthesized to incorporate the functions of a plurality of such peptides in a single peptide.

While specific examples of the peptide or protein for use in accordance with this invention are mentioned below, this does not mean that other known peptides or proteins are excluded. These peptides or proteins may be naturally occurring, recombinant or chemically synthesized substances.

The following is a partial listing of such peptides or proteins. Cytokines, peptide hormones, growth factors, factors acting on the cardiovascular system, cell adhesion factors, factors acting on the central and peripheral nervous systems, factors acting on humoral electrolytes and hemal organic substances, factors acting on bone and skeleton, factors acting on the gastrointestinal system, factors acting on the kidney and urinary organs, factors acting on the connective tissue and skin, factors acting on the sense organs, factors acting on the immune system, factors acting on the respiratory system, factors acting on the genital organs, and various enzymes.

Among preferred peptides or proteins are cytokines, peptide hormones, growth factors, factors acting on the cardiovascular system, factors acting on the central and peripheral nervous systems, factors acting on humoral electrolytes and hemal organic substances, factors acting on bone and skeleton, factors acting on the gastrointestinal system, factors acting on the immune system, factors acting on the respiratory system, factors acting on the genital organs, and enzymes.

The cytokines include tymphokines, monokines, hematopoietic factors and so on.

The lymphokines include interferons (e.g. interferon-$\alpha$, -$\beta$ and -$\gamma$), interleukins (e.g. interleukin 2 through 11) and so on.

The monokines include interleukin-1, tumor necrosis factors (e.g. TNF-$\alpha$ and -$\beta$), malignant leukocyte inhibitory factor (LIF) and so on.

The hematopoietic factors include, among others, erythropoietin, granulocyte colony stimulating factor (G-CSF), granulocyte-macrophage stimulating factor (GM-CSF) and macrophage colony stimulating factor (M-CSF). As factors having hematopoietic activity, factors having thrombopoietic (proliferation) activity, such as a leukocyte proliferation factor preparation (Leucoprol, Morinaga Milk), thrombopoietin, platelet proliferation stimulating factor and megakaryocyte proliferation (stimulating) factor can also be mentioned.

The factors acting on bone and skeleton include bone GLa peptide, parathyroid hormone and its active fragments (osteostatin, Endocrinology 129, 324, 1991), histone H4-related bone formation and proliferation peptide (OGP, The EMBO Journal 11, 1867, 1992) and their muteins, derivatives and analogs thereof.

The growth factors mentioned above include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and so on.

Among the peptide hormones mentioned above are insulin, growth hormone, luteinizing hormone-releasing hormone (LH-RH), adrenocorticotropic hormone (ACTH), amylin, oxytocin, luteinizing hormone and other factors acting on the genital organs and their derivatives, analogs and congeners. As analogs of said LH-RH, such known substances as those described in U.S. Pat. Nos. 4,008,209, 4,086,219, 4,124,577, 4,317,815 and 5,110,904 can be mentioned.

As said factors acting on the cardiovascular system, there can be mentioned factors which control blood pressure, arteriosclerosis, etc., such as endothelins, endothelin inhibitors, endothelin antagonists described in EP 436189, 457195, 496452 and 528312, JP [Laid Open] No. H-3-94692/1991 and 130299/1991, endothelin producing enzyme inhibitors vasopressin, renin, angiotensin I, angiotensin II, angiotensin III, angiotensin I inhibitor, angiotensin II receptor antagonist, atrial naturiuretic peptide (ANP), antiarrythmic peptide and so on.

The factors acting on the central and peripheral nervous systems include opioid peptides (e.g. enkepharins, endorphins, kyotorphins), neurotropic factor (NTF), calcitonin gene-related peptide (CGRP), thyroid hormone releasing hormone (TRH), salts and derivatives of TRH [JP [Laid Open] No. 50-121273/1975 (U.S. Pat. No. 3,959,247), JP [Laid Open] No. 52-116465/1977 (U.S. Pat. No. 4,100,152) ], neurotensin and so on.

Among the factors acting on the gastrointestinal system are secretin and gastrin.

As the factors acting on humoral electrolytes and hemal organic substances, there may be mentioned those factors which control hemagglutination, plasma cholesterol level or metal ion concentrations, such as calcitonin, apoprotein E and hirudin, by way of example. As examples of the cell adhesion factor, there can be mentioned laminin and intercellular adhesion molecule 1 (ICAM 1).

As the factors acting on the kidney and urinary tract, there can be mentioned substances which regulate the function of the kidney, such as brain-derived naturiuretic peptide (BNP), urotensin and so on.

As said factors which act on the sense organs, there can be mentioned factors which control the sensitivity of the various organs, such as substance P.

As said factors acting on the immune system, there can be mentioned factors which control inflammation and malignant neoplasms and factors which attack infective microorganisms, such as chemotactic peptides and bradykinins.

Also included are naturally occurring, chemically synthesized or recombinant peptides or proteins which may act as antigens, such as cedar pollen and ragweed pollen. These factors are administered, either independently, as coupled to haptens, or together with an adjuvant, in the formulations according to the present invention.

As the factors acting on the respiratory system, factors associated with asthmatic responses may be mentioned as examples.

These peptides or proteins may further include enzymes of natural origin and recombinant enzymes, and the enzymes which can be administered include but are not limited to superoxide dismutase (SOD), asparaginase, kallikreins and so on.

The peptides or proteins, in the context of the present invention, cover soluble receptors for such polypeptides.

These peptides or proteins may further include synthetic polymers such as polyethylene glycol, natural polymers such as chondroitin, polysaccharides, etc. and those chemically modified with non-peptide substances. The non-peptide substances mentioned above may be ligands for receptors or antigens for antibodies.

Furthermore, the peptide or protein may be a plurality of peptides joined together by chemical means or by genetic engineering technology.

The peptide or protein which can be used in the present invention further includes parathyroid hormone and its muteins or derivatives which are available from natural sources or obtainable by genetic engineering or chemical means. Also included are active fragments each consisting of 34 amino acids reckoned from the N-terminus of said peptide hormone. One example is the human PTH (1→34) derivative described in JP Application No. 257490/1990, that is a peptide of the following general formula or a salt thereof.

$R_1$-Val-Ser-Glu-Ile-Gln-Leu-$R_2$-His-Asn-$R_3$-$R_4$-$R_5$-His-Leu-Asn-Ser-$R_6$-$R_7$-Arg-$R_8$-Glu-$R_9$-Leu-$R_{10}$-$R_{11}$-$R_{12}$-Leu-Gln-Asp-Val-His-Asn-$R_{13}$   SEQ ID No:1 wherein $R_1$ means Ser or Aib, $R_2$ means Met or a natural type fat-soluble amino acid, $R_3$ means Leu, Ser, Lys or an aromatic amino acid, $R_4$ means Gly or a D-amino acid, $R_5$ means Lys or Leu, $R_6$ means Met or a natural fat-soluble amino acid, $R_7$ means Glu or a basic amino acid, $R_8$ means Val or a basic amino acid, $R_9$ means Trp or 2-(1,3-dithiolan-2-yl)Trp, $R_{10}$ means Arg or His, $R_{11}$ means Lys or His, $R_{12}$ means Lys, Gln or Leu, $R_{13}$ means Phe or Phe-NH$_2$, Excluded, however, is the case in which $R_1$ is Ser, $R_2$ is Met, $R_3$ is Leu, $R_4$ is Gly, D-Ala or D-Pro, $R_5$ is Lys, $R_6$ is Met, $R_7$ is Glu, $R_8$ is Val, $R_9$ is Trp, $R_{10}$ is Arg, $R_{11}$ is Lys and $R_{12}$ is Lys at the same time. (SEQ ID No: 1)

Referring to the above peptide, the natural type fat-soluble (liposoluble) amino acid $R_2$, $R_6$ means a fat-soluble amino acid selected from among the amino acids constituting naturally-occurring (animal, vegetable or microbial) proteins, thus including such species as Leu, Ile, Val, Phe and Trp. The aromatic amino acid $R_3$ includes such species as Phe, β-naphtylAla, Trp and Tyr. The D-smino acid $R_4$ may be virtually any D-amino acid and includes such species as D-Leu, D-Ile, D-Nle, D-Val, D-Ser, D-ser(But), D-Abu, D-Thr, D-Nva, D-Met, β-naphthylD-Ala, D-Trp, D-Tyr, D-Lys, D-Lys(Fmoc), D-Phe and D-Asn. Generally, however, neutral amino acids such as D-Ser, D-Leu, β-naphthylD-Ala, D-Trp, D-Asn, D-Tyr, etc. are preferred. The basic amino acid $R_7$, $R_8$ includes, among others, Arg, Lys, Ash and His. The substitution is not limited to one position but can be a combination of substitutions in a plurality of positions, preferably a combination of substitutions in not more than 3 positions.

As a further example of the peptide having PHT activity, there can be mentioned a human PTH (1→34) derivative of the following general formula or a salt thereof described in JP Application No. 63517/1992.

Ser-Val-$R_1$-Glu-Ile-Gln-Leu-Met-His-Asn-Leu-Gly-Lys-His-Leu-$R_2$-Ser-Met-Glu-Arg-Val-Glu-Trp-Leu-$R_3$-$R_4$-$R_5$-Leu-Gln-Asp-Val-His-Asn-$R_6$   (SEQ ID No:2)

wherein $R_1$ means Ser or a D-α-amino acid containing not more than 4 carbon atoms, $R_2$, $R_3$, $R_4$ and $R_5$ each means a water-soluble α-amino acid, $R_6$ means Phe or PheNH$_2$.

Excluded is the case in which $R_1$ is Ser, $R_2$ is Asn, $R_3$ is Arg or His, $R_4$ is Lys or His, $R_5$ is Lys, Leu or Gln at the same time.

The PTH (1→34) derivative described in WO92/00753 and human PTH fragment in JP (Laid Open) No. 4-247034/1992 can also be the subject peptide of the invention.

The cytidine nucleotide as a moiety of the cytidine nucleotide derivative, as the term is used in the present invention, is a substance available on phosphorylation of one or more -OH groups of the ribose moiety of cytidine and may be any of mono-, di- or tri-phosphates. The derivative as the term is used in this context means a compound available on substitution of at least one oxygen atom of the phosphoric acid moiety of said cytidine nucleotide by a different atom or group. The different atom here may for example be sulfur or nitrogen, while the substituent group includes lower alkyl, lower alkoxy, amide and so on. Included in the derivative are species forming esters with glucose or other sugar or a quaternary ammonium compound such as choline.

The cytidine nucleotide derivative of the present invention may, thus, be any derivative that is physiologically acceptable and has a capacity to promote the absorption of a physiologically active peptide or protein.

The absorption of peptides or proteins may take place via a variety of routes according to their characteristics. For example, a given peptide or protein may find its way through clearances between the cells constituting the mucous membrane and reach the vasuclar wall, while another peptide or protein may, either passively or actively, be taken up in the cells once and then discharged and as it repeats this process finally reaches the vascular wall. The cytidine nucleotide derivative of the present invention may promote the translocation of peptides or proteins along such a route or may act directly on the local mucosal vasuclar wall to promote their absorption. The promotion of absorption is not limited to these mechanisms but the promotion by other mechanisms may also be involved. Moreover, the cytidine nucleotide derivative of the present invention may interact with a peptide or protein to form a complex or conjugate to thereby promote absorption. In any event, the dominant mechanism of promotion of absorption varies subtly according to the characters of the cytidine nucleotide derivatives of the present invention.

As an example, a substance having the generic name of citicoline, the chemical name of cytidine diphosphate choline and the molecular formula of $C_{14}H_{26}N_4O_{11}P_2$ can be mentioned. This substance is a drug developed as the result of biochemical and pharmacological researches into the abnormality of phospholipid metabolism, consciousness, brain function and pathological changes following brain injury and its clinical usefulness in the disturbance of consciousness associated with brain damage, disturbance of consciousness in the acute phase of cerebral infarction, postapoplectic hemiplegia and Parkinson's disease is well documented (c.f. the package insert literature on Nicholine H Injection, Takeda Chemical Industries). Moreover, this substance is also used in a combination therapy with a protease inhibitor in acute pancreatitis, acute exacerbation of chronic recurrent pancreatitis or postoperative acute pancreatitis. This compound is known to inhibit the decomposition of locithin to promote phospholipid biosynthesis and thereby improve phospholipid metabolism. Its safety has been well established by the profusion of clinical experiences. Therefore, a pharmaceutical composition comprising this compound and a physiologically active peptide or protein can be safely administered through the nasal, vaginal or other mucosa.

The weight ratio of the physiologically active peptide or protein to the cytidine nucleotide derivative is preferably 10000:1 through 1:10000, more preferably 100:1 through 01:10000, and most advantageously 10:1 through 1:1000. In the case of a liquid dosage form, for instance, the concentration of the cytidine nucleotide derivative is about 0.01 to 25% (w/v), preferably about 0.1 to 15% (w/v), and more preferably about 0.1 to 10% (w/v). With regard to other dosage forms, the two ingredients are used in the above-mentioned ratio while insuring that the absorption promoting effect of the cytidine nucleotide derivative according to the invention may be well brought into being and yet the physical properties of the particular dosage form will not be adversely affected. The composition of the invention is provided in the pH range which does not remarkably affect the activity of the physiologically active peptide or protein and is physiologically acceptable. The preferred range is about pH 2 to pH 10. The more preferred range is about 3 to pH 9, and the most desirable range is about pH 3.5 to pH 8. Depending on the species of physiologically active peptide or protein used, an acidic side or a basic side is preferred to the neutral for enhanced stability and/or absorption of the peptide.

When the pharmaceutical composition of the invention is a liquid, its tonicity as measured with reference to the tonicity of 0.9% (w/v) physiological saline solution is adjusted to a value at which no irreversible change will be induced in the mucosa at the site of application. The tonicity is adjsuted to generally ⅓ to 3, preferably ½ to 2, and most desirably ¾ to 1.7, with the tonicity of 0.9% (w/v) physiological saline solution being taken as unity.

In the manufacture of a transmucosal therapeutic composition of the present invention, the cytidine nucleotide derivative may be directly blended with the physiologically active peptide or protein or previously incorporated in a hydrophilic, biodegradable or other polymer and then blended with the physiologically active peptide or protein. In certain instances, the derivative may be coated on the surface of a dosage form which is to contact the mucosa or incorporated in the superficial layer of such surface. All that is necessary is that the physiologically active peptide or protein and the cytidine nucleotide derivative should be concurrently brought into contact with the mucosa.

In addition to the above two ingredients, the transmucosal therapeutic composition of the invention generally contains various pharmaceutically acceptable additives as well as a base necessary for dispersion of such substances. Said additives include but are not limited to pH control agents, such as arginine, sodium hydroxide, glycine, hydrochloric acid, citric acid, etc., local anesthetics represented by benzyl alcohol, isotonizing agents such as sodium chloride, mannitol, sorbitol, etc., adsorption inhibitors such as Tween 80 etc., solubilizers such as cyclodextrins and derivatives thereof, stabilizers such as serum albumin etc., and reducing agents such as glutathione and so on.

Since a variety of proteolytic enzymes are present in the mucosa and in the administration atmosphere, there are cases in which a protease inhibitor can be advantageously incorporated in the composition of the invention to preclude degradation of the physiologically active peptide or protein and thereby insure a still enhanced bioavailability. The protease inhibitor mentioned above includes but is not limited to gabaxate mesylate, α1-antitrypsin, aprotinin, leupepsin, α2-macroglobulin, pepstatin and egg white or soybean trypsin inhibitor. These inhibitors can be used alone or in combination. The protease inhibitor may be incorporated in the hydrophilic polymer, coated on the surface of the dosage form which is to contact the mucosa or incorporated in the superficial phase of said surface.

The transmucosal therapeutic composition of the present invention may be further supplemented with an absorption promoter which assists in the absorption and diffusion of the physiologically active peptide or protein. The absorption promoter may be any promoter that is pharmaceutically acceptable. Thus, there can be mentioned sodium salicylate and salicylic acid derivatives (acetyl salicylate, choline salicylate, salicylamide, etc.), amino acids and salts thereof (e.g. monoaminocarboxlic acids such as glycine, alanine, phenylalanine, proline, hydroxyproline, etc., hydroxyamino acids such as serine etc., acidic amino acids such as aspartic acid, glutamic acid, etc. and basic amino acids such as lysine etc., inclusive of their alkali metal or alkaline earth metal salts), N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts), substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters and so on. While the mechanism of absorption promotion may vary with different absorption promotors, the proper one for a long term administration without changing the mucosal membrane can be selected according to each combination of the physiologically active peptide or protein and other ingredients.

The above-mentioned additives may be dispersed in the base or vehicle.

The base for the transmucosal therapeutic composition of the present invention may be a hydrophilic compound having a capacity to disperse the peptide and said additives. The molecular weight of such hydrophilic compound is not less than 1000, preferably not less than 10000 and more preferably not less than 100000. The compound need only be a pharmaceutically acceptable substance and typically includes but is not limited to the following compounds. Thus, copolymers of polycarboxylic acids or salts thereof or carboxylic anhydrides (e.g. maleic anhydride) with other monomers (e.g. methyl (meth)acrylate, acrylic acid, etc.), hydrophilic vinyl polymers such as polyvinyl acetate, polyvinyl alcohol, polyvinylpyrrolidone, etc., cellulose derivatives such as hydroxymethylcellulose, hydroxypropylcellulose, etc., and natural polymers such as chitosan, collagen, sodium alginate, gelatin, hyaluronic acid, etc. and nontoxic metal salts thereof. Further, synthetic fatty acid esters such as polyglycerin fatty acid esters, sucrose fatty acid esters, etc. can also be mentioned.

These hydrophilic polymers can be used alone or in combination and a necessary structural integrity can be imparted by partial crystallization, ionic bonding, crosslinking or the like.

Any of these hydrophilic polymers may be molded into a suppository or film form and applied to the vaginal, rectal or other mucosa. Moreover, they can be molded into microspheres or the like and applied to the mucosa of the nose, vagina or gastrointestinal tract, e.g. gastric mucosa. They may also be applied in powdery form or as a solution (which may be viscous) to the mucosa. The combination of such a hydrophilic polymer and the cytidine nucleotide derivative may result in a further promotion of absorption.

As the base for use in the present invention, a biodegradable synthetic polymer can be employed. The biodegradable polymer typically includes but is not limited to polylactic acid, poly(lactic acid-glycolic acid) copolymer, polyhydroxybutyric acid, poly(hydroxybutyric acid-glycolic acid) copolymer and mixtures thereof. These biodegradable polymers may be molded into a suppository spindle or a film for application to the vaginal or rectal mucosa. It is also possible to process the biodegradable polymer into microcapsules (microspheres) or nanocapsules (nanospheres) in the per se known manner, disperse them in a biocompatible dispersing medium and apply the dispersion to the nasal, vaginal or digestive tract, e.g. rectal, mucosa. The physiologically acceptable peptide is dispersed in such a dosage form base in the per se known manner. The release of the active peptide from such a dosage form may be by diffusion, disintegration of said biodegradable polymer or the associated formulation of water channels. A further possible mechanism is that when the glass transition temperature of such a biodegradable polymer is near or lower than the body temperature, the biodegradable polymer applied to the living body becomes softened to cause the release of the physiologically active peptide at an accelerated rate of diffusion. A further promotion of absorption may be insured by an ingenious combination of biodegradable polymer and cytidine nucleotide derivative.

As a further alternative, it is possible to disperse the active peptide in microcapsules (microspheres) or nanocapsules (nanospheres) prepared from a polymer other than those mentioned above, then disperse them in a biocompatible dispersing medium and apply the dispersion to the nasal, vaginal or digestive tract, e.g. rectal, mucosa. For example, Michael et al. (Journal of Pharmacy and Pharmacology, 43, 1–5, 1991) report that when insulin is entrapped in isobutyl 2-cyanoacrylate nanocapsules and applied to the mucosa at varying sites of the digestive tract, the hypoglycemic action is sustained over a protracted time. By using these nanocapsules in combination with the cytidine nucleotide derivative, a further promotion of absorption can be realized.

While the above-mentioned polymer generally functions as a pharmaceutical base, it is preferable to add a different base which is commonly used in the manufacture of dosage forms, in accordance with the particular dosage form to be manufactured. Taking rectal or vaginal suppositories as an example, witepsols, cacao butter, macrogols, propylene glycol, glycerin, etc. can be used where necessary.

The pharmaceutical composition of the present invention may contain a hydrophilic low molecular weight compound. Such a hydrophilic low molecular weight compound provides continuous passages through which the water-soluble physiologically active peptide or protein may diffuse through the base to the body surface where it is absorbed. The passageways may be either microscopic or macroscopic, that is to say the whole dosage form may serve as a passageway.

The hydrophilic low molecular weight compound can be any such compound that absorbs moisture from the mucosa or the administration atmosphere and dissolves the water-soluble active peptide. The molecular weight of said hydrophilic low molecular weight compound is not more than 10000 and preferably not more than 3000. Thus, as polyol compounds, there can be mentioned oligo-, di- and monosaccharides such as sucrose, mannitol, lactose, L-arabinose, D-erythrose, D-ribose, D-xylose, D-mannose, D-galactose, lactulose, cellobiose, gentibiose, etc. can be mentioned. As other polyol compounds, there can be mentioned glycerin and polyethylene glycol (average molecular weight 200–3000). Other examples of said hydrophilic low molecular weight compound include N-methylpyrrolidone, alcohols (e.g. oligovinyl alcohol, ethanol, ethylene glycol, propylene glycol, etc.). These hydrophilic low molecular weight compounds are used alone or in combination.

The above-mentioned hydrophilic polymer, biodegradable polymer, hydrophilic low molecular weight compound, absorption promoter, protease inhibitor and additives are preferably selected according to the amino acid composition of the active peptide, the steric structure thereof and other factors.

The amount of the physiologically active peptide or protein to be contained in the transmucosal therapeutic composition of the present invention can be selected according to the activity of the particular substance and its therapeutically effective dose but in consideration of the fact that the bioavailability of any active substance can never be 100%, that is to say the administered dose of the active peptide is not completely absorbed, it is preferable to incorporate a slightly larger amount than the usual dosage. Where the dosage form is an aerosol or the like which is repeatedly dispensed from the same container, it is recommendably so arranged that the unit dose will be slightly greater than the usual dose. It should be understood that the dosage should vary with species of warm-blood animals such as man, domestic animals, etc. and their body weights.

The transmucosal therapeutic composition of the present invention before unsealing is stored at room temperature or preferably in the cold. The room temperature and cold mentioned above are both defined in the Japanese Pharmacopoeia. When a plurality of unit doses are dispensed from the same container, it is necessary to somehow prevent contamination at administration, such as a device for precluding the backflow of the body fluid into the dispensing container, preferably in combination with storage in the cold after each dispensing. For the prevention of multiplication of adventitious microorganisms within the container, a pharmaceutically acceptable preservative or/and an antimicrobial agent may be added to the composition.

While the transmucosal therapeutic composition of the invention is applied to the mucosa, the sites of administration may be the same as those used for the usual transmucosal therapeutic preparations. Generally the nasal or vaginal mucosa is the favorite site of administration but the composition can be applied to the rectal, small intestinal or oral mucosa. According to the species of physiologically active peptide or protein used, the dosage form and the site of administration, a specific administration method can be selected. Some typical methods of administration are now described below, although these are by no means exclusive choices.

When the dosage form to be manufactured is a solution, a solution of the physiologically active peptide or protein in water or physiological saline where the cytidine nucleotide derivative is added or a solution of a vacuum-dried or freeze-dried preparation containing both the physiologically active peptide or protein and the cytidine nucleotide derivative in water or physiological saline can be sprayed from a nebulizer or other suitable spray means. It is also possible to add sodium alginate, sodium hyaluronate, hydroxypropylcellulose or the like to the solution to make it viscous so as to prolong the local residence time of the composition.

When the composition of the invention is provided as a solution or a microfine powder, a suitable atomizer or the like may be provided to insure a sufficient reduction of particle size for effective inhalation from the nasal or oral cavity so that the drug may successfully reach the lungs (pulmonary mucosa). Moreover, if the sterility and other pharmaceutical requirements for parenteral products are met, the composition may be administered intravascularly or subcutaneously.

When the dosage form is a rectal suppository, it is inserted from the anus with fingers. The vaginal suppository is inserted into the vagina with fingers or a pertinent applicator. For oral administration of nanocapsules, they are packed into a conventional gelatin capsule shell for oral administration. It is also possible to utilize a drug delivery system such that an enteric coating is applied to said gelatin capsule to cause the nanocapsules to be released only in the duodenum or inferiorly thereof, not in the stomach. It is also possible to add a liquid for oral administration, for example an isotonic saline solution or a syrup, to the above nanocapsules either as they are or as carrying an enteric coating and administer the resulting suspension.

It is known that in postmenopausal women, in whom the secretion of female hormone is suppressed, the vaginal mucosa is decreased in thickness to become more permeable to drugs. The composition of the invention can be used with advantage for the vaginal administration of peptides such as calcitonin, parathyroid hormone and their active fragments and derivatives in the treatment of osteroporosis and other diseases which are frequent in postmenopausal women.

EXAMPLES

The following reference and working examples are merely illustrative of the invention and should by no means be construed as defining the scope of the invention. Experimental examples are also presented below to illustrate the efficacy of the transmucosal therapeutic composition of the invention.

Reference Example 1

Synthesis and purification of a PTH partial peptide (1–34) analog

Synthesis of this peptide was carried out by a modified method for solid phase peptide synthesis which was originally developed by Merrifield (R. B., Merrifield, Advances in Enzymology 32, 221–296, 1969) using an automatic peptide synthesizer 430A (Applied Biosystems). Synthesis of the protected peptide-resin was carried out in accordance with the protocol designated by Applied Biosystems. To obtain a derivative having a free C-terminal carboxyl group, a protected amino acid-p-oxymethylphenylacetamidomethyl resin (polystyrene-1% divinylbenzene) was used as the starting material, while 4-methylbenzhydryl-resin was used as the starting material when a carboxylamide derivative was to be obtained. The protected amino acids were serially condensed to the above starting material. For the protection of the α-amino group of each amino acid prior to condensation, the tert-butyloxycarbonyl (BOC) group was used. Side chain functional groups were protected as follows. The hydroxyl group of serine or threonine was protected in the form of o-benzyl ether, the hydroxyl group of tyrosine in the form of p-bromobenzyloxycarbonyl ester, the carboxyl group of glutamic acid or aspartic acid in the form of benzyl ester, the imidazole nitrogen of hystidine with benzyloxy methyl, the side-chain amino group of lysine with 2-chlorobenzyloxycarbonyl, the guanidino group of arginine with p-toluenesulfonyl, and the indoleimine group of tryptophan with formyl. All the amino acids were obtained from Applied Biosystems Japan or Bachem Chemicals.

After all the amino acids had been condensed on the resin, the protected peptide-resin was taken out from the synthesizer and dried. The peptide-resin (1 g) was reacted with anhydrous hydrogen fluoride (8 ml) containing p-cresol (1 ml), 1,2-ethanedithiol (1 ml) and 2-mercaptopyridine (100 mg) at 0° C. for 2 hours. The hydrogen fluoride was then distilled off and the residue was washed with diethyl ether to remove most of the reagent mixture. The peptide was extracted with 3% acetic acid (10 ml) and the resin was filtered off. The filtrate was purified by gel filtration using Sephadex G-25. The conditions of gel filtration were: column size=2.8×60 cm, detection wavelength=230 or 280 nm, solvent=3% acetic acid and flow rate 40 ml/hr. The peptide-containing fractions were pooled and lyophilized and the resulting powder was further purified by reversed phase high performance liquid chromatography. The conditions were: column=YMC-Pack A-324 ODS (10×250 mm), eluent A=0.1% trifluoroacetic acid-99.9% $H_2O$, eluent B=0.1% trifluoroacetic acid-99.9% acetonitrile, gradient elution program=0 min (90% A+10% B) and 30 min (60% A+40% B) [where necessary, a different elution program can be used], elution speed=1.6 ml/min, detection wavelength=230 or 280 nm. The fractions rich in the pure product were pooled and passed through a Biorad AGI×8 (acetate form, 1.8×5 cm) column and the eluate was collected. After the removal of acetonitrile by distillation, the residue was lyophilized.

Example 1

In 600 µl of physiological saline for injection (Fuso Pharmaceutical) was dissolved 4 mg of the active fragment corresponding to the N-terminal through amino acid in 34-position of human PTH as prepared by the procedure described in Reference Example 1. A 90 µl portion of this solution was blended with 90 µl of Nicholin H Injection (Takeda Chemical Industries) containing 500 mg of citicoline in each 2 ml.

Example 2

In 600 µl of physiological saline for injection (Fuso Pharmaceutical) was dissolved 4 mg of human PTH (composed of 84 amino acids) (Bachem). A 100 µl portion of this solution was blended with 100 µl of Nicholin H Injection (Takeda Chemical Industries) containing 500 mg of citicoline in each 2 ml.

Example 3

In 600 µl of physiological saline for injection (Fuso Pharmaceutical) was dissolved 4 mg of an active fragment corresponding to the N-terminal through amino acid in 34-position of human PTH as prepared by the procedure described in Reference Example 1 (solid phase synthesis). A 50 µl of this solution was blended with 50 µl of Nicholin H Injection (Takeda Chemical Industries) containing 500 mg of citicoline in each 2 ml.

Example 4

In 200 µl of physiological saline for injection (Fuso Pharmaceutical) was dissolved 4 mg of human PTH (composed of 84 amino acids) (Bachem). A 50 µl of this solution was blended with 50 µl of Nicholin H injection (Takeda Chemical Industries) containing 500 mg of citicoline in each 2 ml.

Example 5

In 154 µl of physiological saline for injection (Fuso Pharmaceutical) was dissolved 18.47 mg of a PTH active fragment composed of amino acids Nos. 1 to 34 of human PTH as prepared by the procedure of Reference Example 1. A 5 µl portion of this solution was blended with 50 µl of Nicholin H Injection containing 500 mg/2 ml of citicoline (Takeda Chemical Industries) and 45 µl of physiological saline for injection. This composition is administered, 5 µl per animal, into the nasal cavity of rats.

Example 6

In 154 µl of physiological saline for injection (Fuso Pharmaceutical) was dissolved 18.47 mg of a PTH active fragment composed of amino acids Nos. 1 to 34 of human PTH as prepared by the procedure of Reference Example 1. A 50 µl portion of this solution was blended with 50 µl of Nicholin H Injection containing 500 mg/2 ml of citicoline (Takeda Chemical industries). This composition is administered, 5 µl per animal, into the nasal cavity of rats.

Example 7

In 50.75 µl of physiological saline for injection (Fuso Pharmaceutical) was dissolved 2.03 mg of a PTH active fragment composed of amino acids Nos. 1 to 34 of human PTH as prepared by the procedure of Reference Example 1. A 20 µl portion of this solution was blended with 20 µl of Nicholin H Injection containing 500 mg/2 ml of citicoline (Takeda Chemical Industries).

Example 8

In 154 µl of physiological saline for injection (Fuso Pharmaceutical) was dissolved 18.47 mg of a PTH active fragment composed of amino acids Nos. 1 to 34 of human PTH as prepared by the procedure of Reference Example 1. A 5 µl portion of this solution was blended with 50 µl of Nicholin H Injection containing 500 mg/2 ml of citicoline (Takeda Chemical Industries) and 45 µl of physiological saline for injection.

Example 9

In 154 µl of physiological saline for injection (Fuso Pharmaceutical) was dissolved 18.47 mg of a PTH active fragment composed of amino acids Nos. 1 to 34 of human PTH as prepared by the procedure of Reference Example 1. A 50 µl portion of this solution was blended with 50 µl of Nicholin H Injection containing 500 mg/2 ml of citicoline (Takeda Chemical Industries).

Example 10

In 350 µl of physiological saline for injection (Fuso Pharmaceutical) was dissolved 14 mg of a PTH active fragment composed of amino acids Nos. 1 to 34 of human PTH as prepared by the procedure of Reference Example 1. A 50 µl portion of this solution was blended with 25 µl of Nicholin H Injection containing 500 mg/2 ml of citicoline (Takeda Chemical Industries) and 25 µl of physiological saline for injection.

Example 11

In 350 µl of physiological saline for injection (Fuso Pharmaceutical) was dissolved 14 mg of a PTH active fragment composed of amino acids Nos. 1 to 34 of human PTH as prepared by the procedure of Reference Example 1. A 50 µl portion of this solution was blended with 10 µl of Nicholin H injection containing 500 mg/2 ml of citicoline (Takeda Chemical Industries) and 40 µl of physiological saline for injection.

Example 12

In 350 µl of physiological saline for injection (Fuso Pharmaceutical) was dissolved 14 mg of a PTH active fragment composed of amino acids Nos. 1 to 34 of human PTH as prepared by the procedure of Reference Example 1. A 50 µl portion of this solution was blended with 5 µl of Nicholin H Injection containing 500 mg/2 ml of citicoline (Takeda Chemical Industries) and 45 µl of physiological saline for injection.

Example 13

In 195 μl of physiological saline for injection (Fuso Pharmaceutical) was dissolved 7.8 mg of a PTH active fragment composed of amino acids Nos. 1 to 34 of human PTH as prepared by the procedure of Reference Example 1. A 50 μl portion of this solution was blended with 50 μl of Nicholin H Injection containing 500 mg/2 ml of citicoline (Takeda Chemical Industries).

Example 14

20 mg of interferon 2α was dissolved in 0.5 ml of physiological saline for injection. A 50 μl portion of this solution was blended with 50 μl of Nicholin H injection containing 500 mg/2 ml of citicoline (Takeda Chemical Industries).

Example 15

In 155.5 μl of 1/10M citric acid buffer (pH 3.5) was suspended 16.75 mg of human insulin (Wako Pure Chemical Industries). A 20 μl of this suspension was blended with 50 μl of Nicholin H Injection containing 500 mg/2 ml of citicoline (Takeda Chemical Industries).

Test Example 1

In 600 μl of physiological saline for injection (Fuso Pharmaceutical) was dissolved 4 mg of an active fragment (synthesized by solid phase method) corresponding to the N-terminal through amino acid in 34-position of human PTH (Comparative Composition 1).

Figure 1:
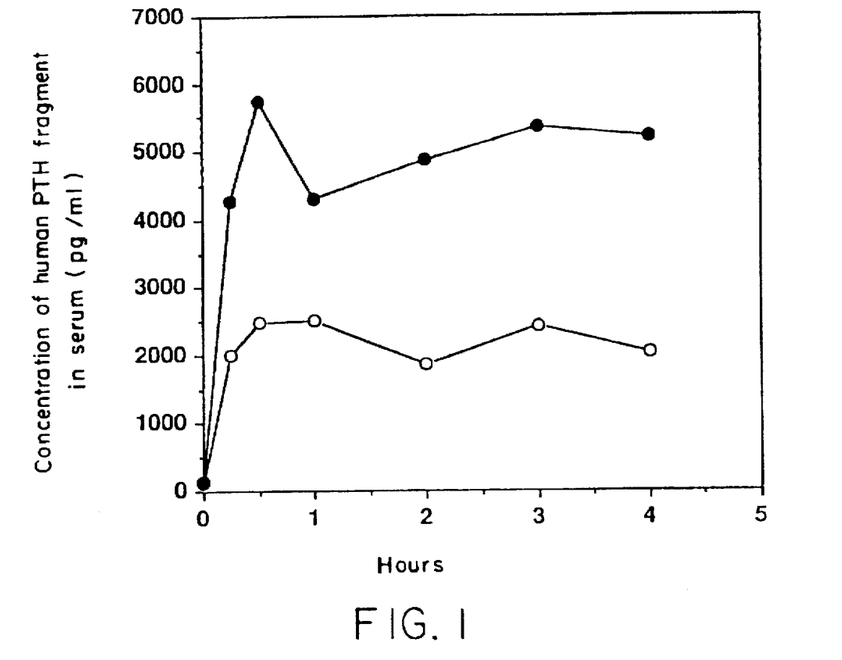
FIG. 1 shows the time course of serum concentration of a human PTH active fragment.

Male SD rats (8 weeks old) were anesthetized with pentobarbital (Nembutai injection, Dainippon Pharmaceutical) and operated on for transnasal dosing in accordance with the procedure described in International Journal of Pharmaceutics 7, p. 317 (1981). Then, using a micropipet (Excelmidegi 8000, D-5, Sanko Pure Chemical), 30 μl of the composition obtained in Example 1 or Comparative Composition 1 was directly administered into the nasal cavity of rats. The blood was serially sampled from the tail vein and the serum concentration of the active human PTH fragment was determined. The time course of the human PTH active fragment in the serum is shown in (FIG. 1). In the group treated with Comparative Composition 1 (○), the serum concentration began to rise 30 minutes after administration and maintained a substantial plateau up to 6 hours after administration. On the other hand, in the group given the composition of Example 1 (●), the serum concentration rose as rapidly as in the group given Comparative Composition 1 but its level was about 2-fold as high and this high value persisted up to 6 hours after administration. This fact indicates that the presence of citicoline results in accelerated absorption of the human PTH active fragment from the nasal mucosa.

Test Example 2

In 600 μl of physiological saline for injection (Fuso Pharmaceutical) was dissolved 4 mg of human PTH (composed of 84 amino acids, Bachem) (Comparative Composition 2).

Figure 2:
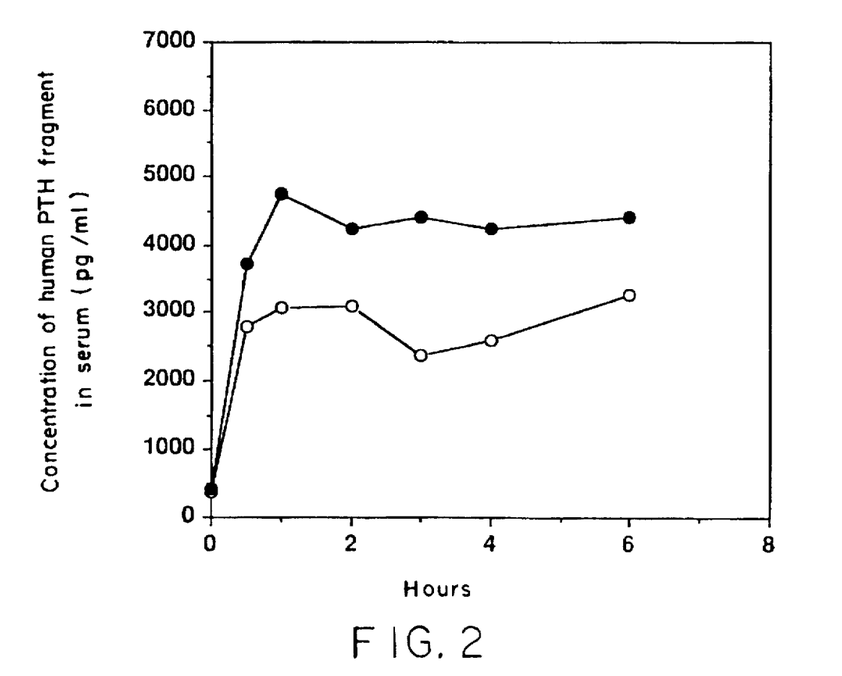
FIG. 2 shows the time course of serum concentration of human PTH.

Male SD rats (8 weeks old) were anesthetized with pentobarbital (Nembutal Injection, Dainippon Pharmaceutical) and operated on for transnasal dosing in accordance with the procedure described in international journal of Pharmaceutics 7, 317 (1981). Then, using a micropipet (Excelmidegi 8000, D-5, Sanko Pure Chemical), 30 μl of the composition obtained in Example 2 or Comparative Composition 2 was directly administered into the nasal cavity of rats. The blood was serially sampled from the tail vein and the serum concentration of human PTH was determined. The time course of human PTH concentration in the serum is shown in (FIG. 2). In the group treated with Comparative Composition 2 (○), the serum concentration began to rise 30 minutes after administration and maintained a substantial plateau up to 6 hours after administration. On the other hand, in the group given the composition of Example 2 (●), which contained citicoline, the serum concentration rose as rapidly as in the group given Comparative Composition 2 but its level was about 2-fold as high and this high value persisted up to 6 hours after administration. This fact indicates that the presence of citicoline results in accelerated absorption of human PTH from the nasal mucosa.

Test Example 3

Figure 3:
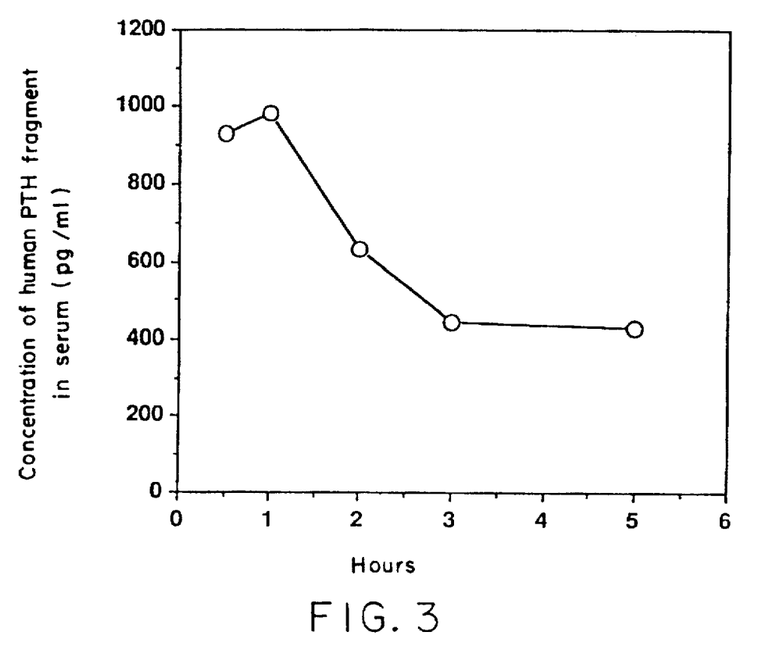
FIG. 3 shows the time course of serum concentration of a human PTH active fragment.

Female SD rats (7 weeks old) were anesthetized with pentobarbital (Nembutal Injection, Dainippon Pharmaceutical) and poly(lactic acid-glycolic acid) microcapsules containing about 1 mg of leuprolerin acetate, an analog of luteinizing hormone releasing hormone, were administered subdermally in the occipital region. Starting the following day, the sexual cycle was monitored by microscopic examination of Giemsa-stained vaginal discharges. After confirming alignment of sexual cycle in all the rats to diestrus, 10 μl of the composition of Example 3 was intravaginally administered from a micropipet (Excelmidegi 8000, D-5, Sanko Pure Chemical) to rats under pentobarbital (Nembutal Injection, Dainippon Pharmaceutical) anesthesia. The blood was serially sampled from the tail vein and the serum concentration of the human PTH active fragment was determined. The time course of serum concentration of the human PTH active fragment is shown in (FIG. 3). It is apparent that the presence of citicoline results in absorption of the human PTH active fragment from the vaginal mucosa.

Test Example 4

Figure 4:
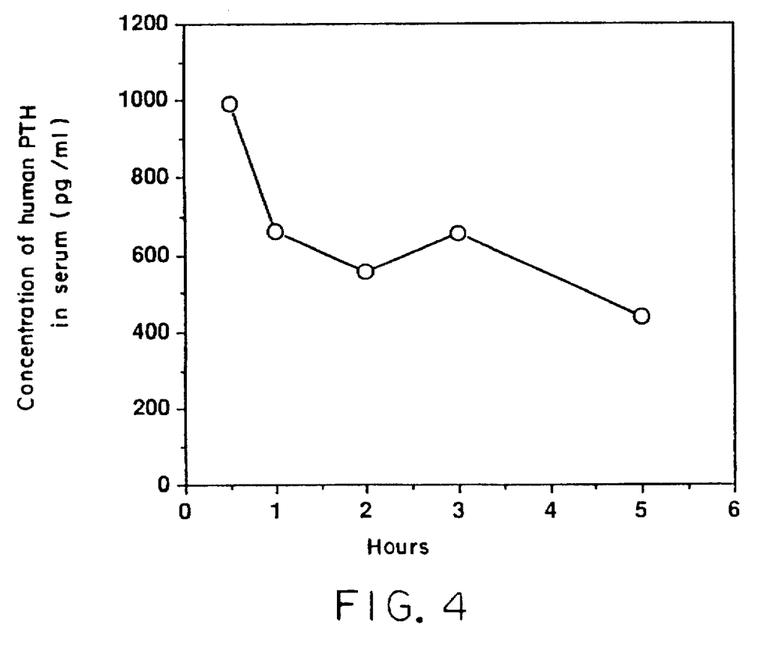
FIG. 4 shows the time course of serum concentration of human PTH.

Female SD rats (7 weeks old) were anesthetized with pentobarbital (Nembutal Injection, Dainippon Pharmaceutical) and poly(lactic acid-glycolic acid) microcapsules containing about 1 mg of leuprolerin acetate, an analog of luteinizing hormone releasing hormone, were administered subdermally in the occipital region. Starting the following day, the sexual cycle was manitored by microscopic examination of Giemsa-stained vaginal discharges. After confirming alignment of sexual cycle in all the rats to diestrus, 10 μl of the composition of Example 4 was intravaginally administered from a micropipet (Excelmidegi 8000, D-5, Sanko Pure Chemical) to rats under pentobarbital (Nembutal Injection, Dainippon Pharmaceutical) anesthesia. The blood was serially sampled from the tail vein and the serum concentration of human PTH was determined. The time course of serum concentration of human PTH is shown in (FIG. 4). It is apparent that the presence of citicoline results in the absorption of human PTH from the vaginal mucosa.

Test Example 5

In 50.75 μl of physiological saline for injection (Fuso Pharmaceutical) was dissolved 2.03 mg of the PTH active fragment composed of amino acids 1 to 34 of human PTH as prepared by the procedure of Reference Example 1. To 20

µl of this solution was added 20 µl of physiological saline for injection (Comparative Preparation 3).

Figure 5:
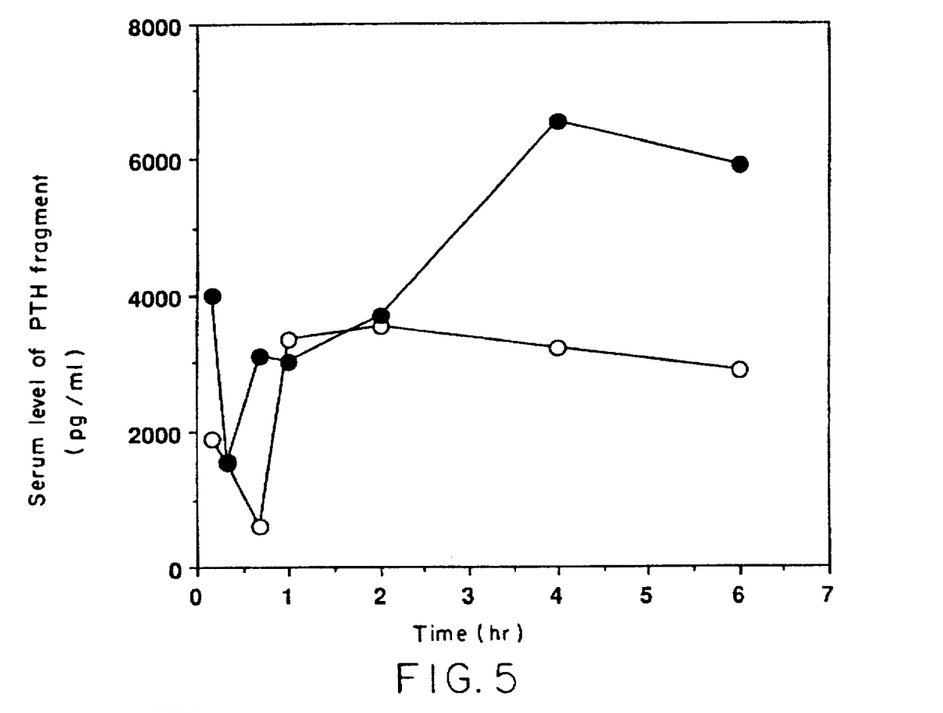
FIG. 5 shows the time course of serum concentration of a human PTH active fragment.

Male SD rats (8 weeks old) were used. Under light anesthesia with pentobarbital (Somnopentyl, Pitman-Moore) (ca. 0.2 ml/rat), 5 µl of the preparation of Example 7 or Comparative Preparation 3 was administered directly into one nostril. For administration, the exclusive micropipet tip (Excelmidigi 8000, D-5, Sanko Junyaku) was inserted far enough into the nostril. After recovery from anesthesia (in just less than about 1 hour), the rats were returned to feeding cages and allowed food and water ad libitum. The blood was serially collected from the tail vein and the serum concentration of the human PTH active fragment was determined. The time course of serum concentration of the human PTH active fragment is shown in (FIG. 5).

In the group (○) given Comparative Preparation 3, the serum concentration showed a minor peak immediately following administration, then rose gradually and remained almost constant from hour 1 to hour 6 after administration. In the group (●) given the citicoline-containing preparation of Example 7, the serum concentration showed a similar minor peak immediately after administration and then continued to rise till 3 hours, when the level was about twice the level in the group given Comparative Preparation 3. These results indicate that even in the normal rat not undergoing surgery, the inclusion of citicoline promotes absorption of human PTH active fragment from the nasal mucosa.

Test Example 6

In 154 µl of physiological saline for injection (Fuso Pharmaceutical) was dissolved 18.47 mg of the PTH active fragment composed of amino acids 1 to 34 of human PTH as prepared by the procedure of Reference Example 1. To 5 µl of this solution was added 95 µl of physiological saline for injection (Comparative Preparation 4).

Figure 6:
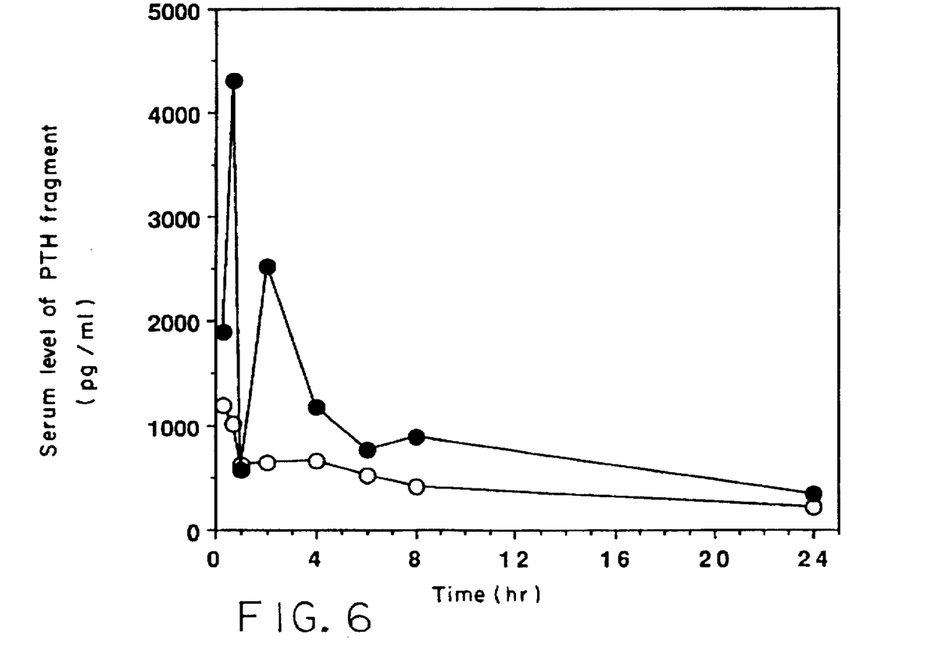
FIG. 6 shows the time course of serum concentration of a human PTH active fragment.

Male SD rats (8 weeks old) were subjected to light anesthesia with pentobarbital (Somnopentyl, Pitman-Moore) (ca. 0.2 ml/rat) and 5 µl of the preparation of Example 8 or Comparative Preparation 4 was administered directly into one nostril. For administration, the exclusive micropipet tip (Excelmidigi 8000, D-5, Sanko Junyaku) was inserted far enough into the nostril. After recovery from anesthesia (in just less than about 1 hour), the rats were returned to feeding cages and allowed food and water ad libitum. The blood was serially collected from the tail vein and the serum concentration of the human PTH active fragment was determined. The time course of serum concentration of the human PTH active fragment is shown in (FIG. 6).

In the group (○) given Comparative Preparation 4, the serum concentration showed a minor peak immediately following administration, then decreased gradually. On the other hand, in the group (●) given the citicoline containing preparation of Example 8, the serum concentration showed peaks immediately and 2 hours following administration, then decreased gradually. The calculated mean bioavailability for the group given citicoline containing preparation was about 100%, subcutaneous administration of PTH active fragments at the same dose being a standard. The results indicate that even in the normal rat not undergoing surgery, the inclusion of citicoline promotes absorption of human PTH active fragment from the nasal mucosa.

Test Example 7

In 154 µl of physiological saline for injection (Fuso Pharmaceutical) was dissolved 18.47 mg of the PTH active fragment composed of amino acids 1 to 34 of human PTH as prepared by the procedure of Reference Example 1. To 50 µl of this solution was added 50 µl of physiological saline for injection (Comparative Preparation 5).

Figure 7:
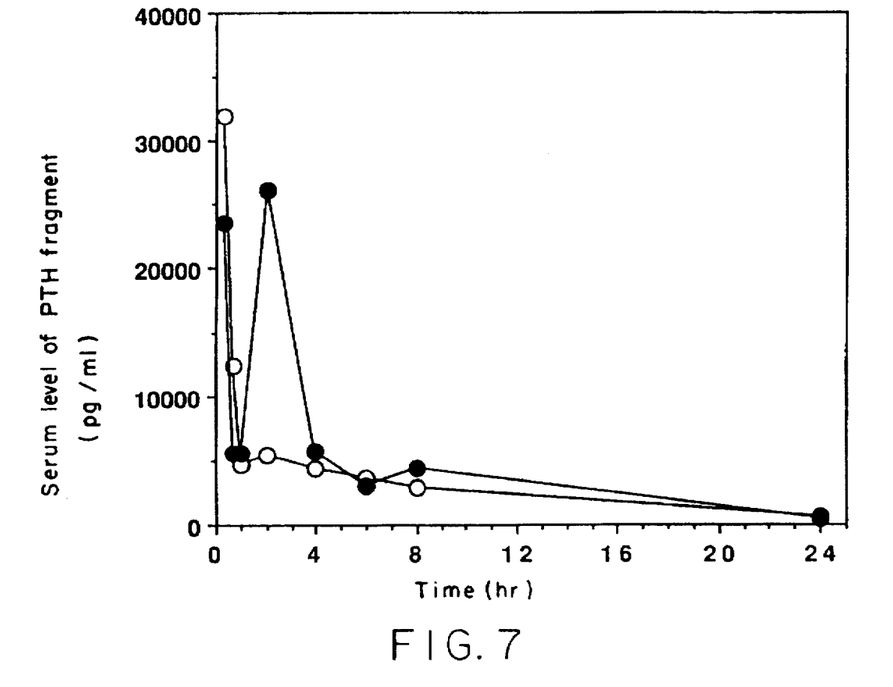
FIG. 7 shows the time course of serum concentration of a human PTH active fragment.

Male SD rats (8 weeks old) were subjected to light anesthesia with pentobarbital (Somnopentyl, Pitman-Moore) (ca. 0.2 ml/rat) and 5 µl of the preparation of Example 9 or Comparative Preparation 5 was administered directly into one nostril. For administration, the exclusive micropipet tip (Excelmidigi 8000, D-5, Sanko Junyaku) was inserted far enough into the nostril. After recovery from anesthesia (in just less than about 1 hour), the rats were returned to feeding cages and allowed food and water ad libitum. The blood was serially collected from the tail vein and the serum concentration of the human PTH active fragment was determined. The time course of serum concentration of the human PTH active fragment is shown in (FIG. 7).

In the group (○) given Comparative Preparation 5, the serum concentration showed a peak immediately following administration, then decreased gradually. On the other hand, in the group (●) given the citicoline containing preparation of Example 9, the serum concentration showed peaks immediately and 2 hours following administration, then decreased gradually. These results indicate that even in the normal rat not undergoing surgery, the inclusion of citicoline promotes absorption of human PTH active fragment from the nasal mucosa.

Test Example 8

In 350 µl of physiological saline for injection (Fuso Pharmaceutical) was dissolved 14 mg of the PTH active fragment composed of amino Nos. 1 to 34 of human PTH as prepared by the procedure of Reference Example 1. To 50 µl of this solution was added 50 µl of physiological saline for injection (Comparative Preparation 6).

Figure 8:
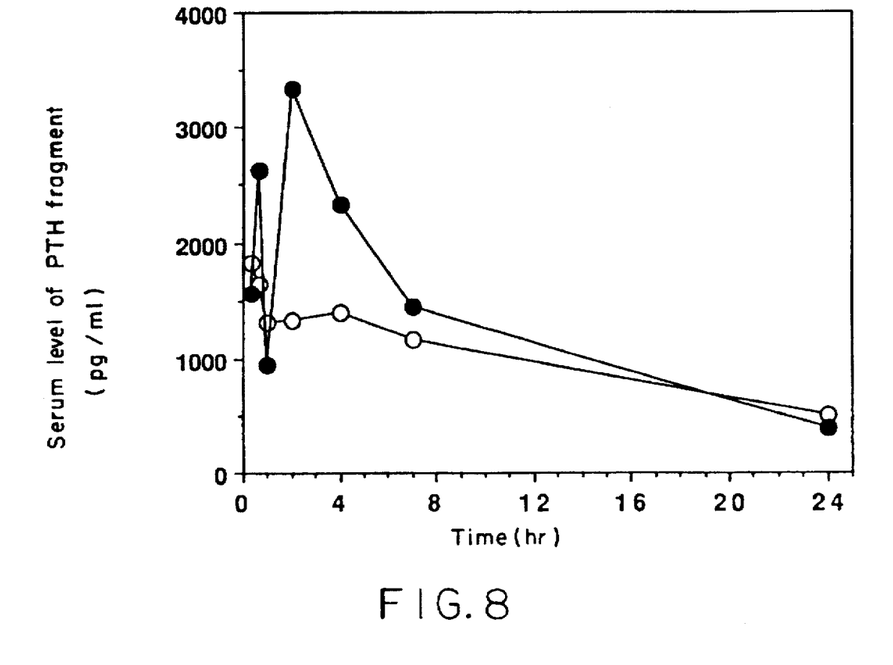
FIG. 8 shows the time course of serum concentration of a human PTH active fragment.

Male SD rats (8 weeks old) were subjected to light anesthesia with diethyl ether and 5 µl of the preparation of Example 10 or Comparative Preparation 6 was administered directly into one nostril (dosage 100 µg/rat). For administration, the exclusive micropipet tip (Excelmidigi 8000, D-5, Sanko Junyaku) was inserted far enough into the nostril. After recovery from anesthesia (in just less than about 15 minutes), the rats were returned to feeding cages and allowed food and water ad libitum. The blood was serially collected from the tail vein and the serum concentration of the human PTH active fragment was determined. The time course of serum concentration of the human PTH active fragment is shown in (FIG. 8). In the group (○) given Comparative Preparation 6, an absorption peak appeared immediately after administration but the serum concentration declined gradually thereafter. On the other hand, in the group (●) given the citicoline-containing preparation of Example 10, an absorption peak which appeared immediately after administration was followed by another peak at hour 2 after administration and, then, the serum concentration declined gradually. These results indicate that even in the normal rat not undergoing surgery, the inclusion of citicoline promots absorption of the human PTH active fragment from the nasal mucosa.

Test Example 9

In 195 µl of physiological saline for injection (Fuso Pharmaceutical) was dissolved 7.8 mg of the PTH active fragment composed of amino acids 1 to 34 of human PTH as prepared by the procedure of Reference Example 1. To 50

μl of this solution was added 50 μl of physiological saline for injection (Comparative Preparation 7).

Figure 9:
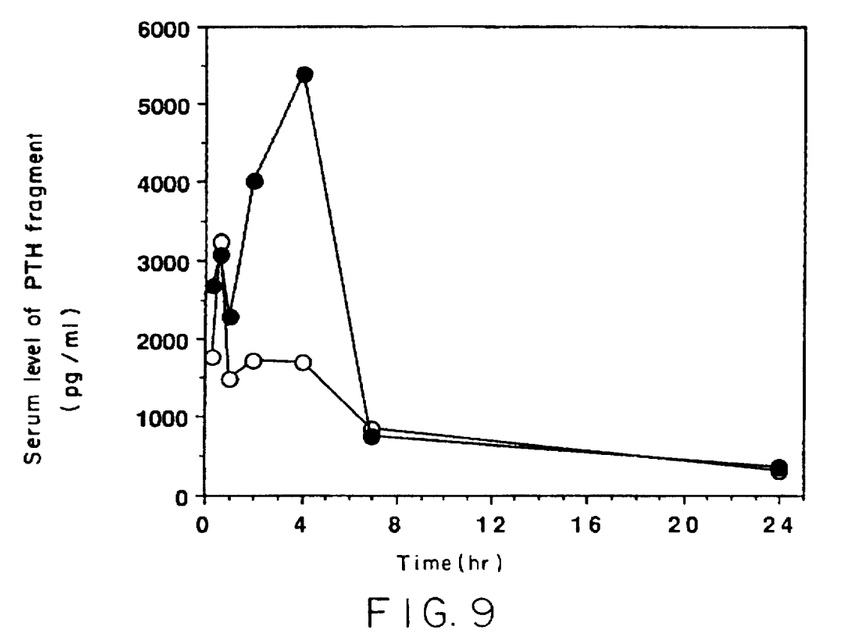
FIG. 9 shows the time course of serum concentration of a human PTH active fragment.

Male SD rats (8 weeks old) were used. With the head fixed in conscious state, 5 μl of the preparation of Example 13 or Comparative Preparation 7 was administered directly into one nostril (dosage 100 μg/rat). For administration, the exclusive micropipet tip (Excelmidigi 8000, D-5, Sanko Junyaku) was inserted far enough into the nostril. After administration, the rats were returned to feeding cages and allowed food and water ad libitum. The blood was serially collected from the tail vein and the serum concentration of the human PTH active fragment was determined. The time course of serum concentration of human PTH active fragment is shown in (FIG. 9).

In the group (○) given Comparative Preparation 7, an absorption peak appeared immediately after administration but the serum concentration declined gradually thereafter. On the other hand, in the group (●) given the citicoline-containing preparation of Example 13, an absorption peak which appeared immediately after administration was followed by another peak at hour 4 after administration and, then, the serum concentration declined gradually. These results indicate that even in the conscious normal rat not undergoing surgery, the inclusion of citicoline promots absorption of the human PTH active fragment from the nasal mucosa.

Test Example 10

Twenty (20) milligrams of interferon α2a (the content of which was assayed by enzyme immunoassay using an interferon preparation containing 3000000 IU (equivalent to ca. 100 μg) of interferon α2a and 5 mg of human serum albumin (Canferon A300, Takeda Chemical Industries) in 1 ml of distilled water for injection as the standard) was dissolved in 0.5 ml of physiological saline for injection and 50 μl of this solution was blended with 50 μl of physiological saline for injection (Comparative Preparation 8).

Figure 10:
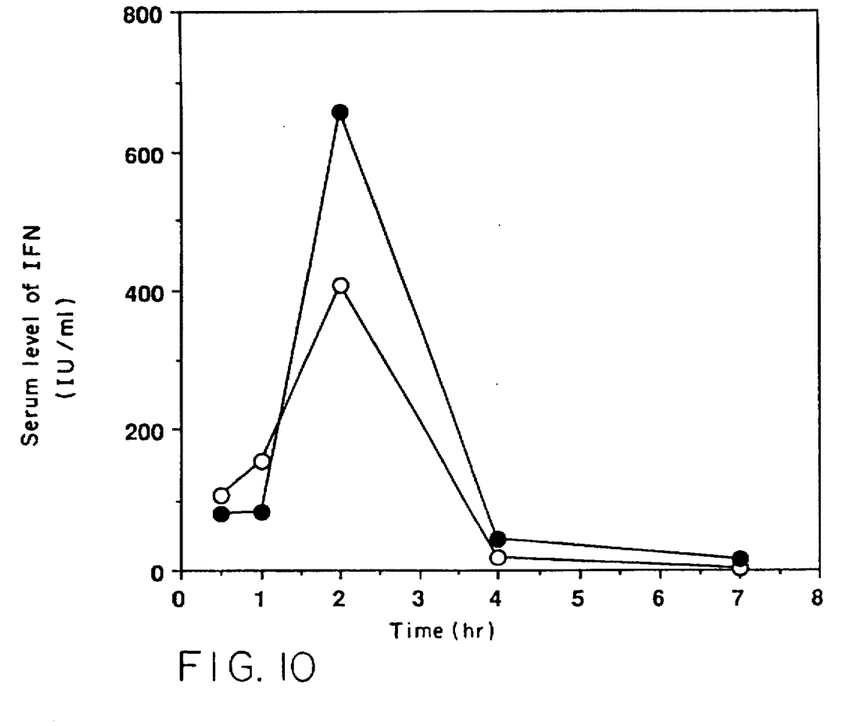
FIG. 10 shows the time course of serum concentration of interferon α.

Male SD rats (8 weeks old) were subjected to light anesthesia with diethyl ether and 5 μl of the preparation of Example 14 or Comparative Preparation 8 was administered directly into one nostril (dosage 100 μg/rat). For administration, the exclusive micropipet tip (Excelmidigi 8000, D-5, Sanko Junyaku) was inserted far enough into the nostril. After recovery from anesthesia (in just less than about 15 minutes), the rats were returned to feeding cages and allowed food and water ad libitum. The blood was serially collected from the tail vein and the serum concentration of human interferon α was determined. The time course of serum concentration of human interferon α is shown in (FIG. 10).

In the group (○) given Comparative Preparation 8, the serum concentration reached a peak at hour 2 but then declined. In the group given the citicoline-containing preparation of Example 14 (●), the serum concentration also peaked at hour 2 and then declined but the peak was higher and the area under the blood concentration-time curve (AUC) was also about 1.5-fold as high in the group treated with the preparation of Example 14.

Test Example 11

In 155.5 μl of 1/10M citrate buffer (pH 3.5) was dispersed 16.75 mg of human insulin (Wako Pure Chemical) and 50 μl of this dispersion was blended with 50 μl of physiological saline for injection (Comparative Preparation 9).

Figure 11:
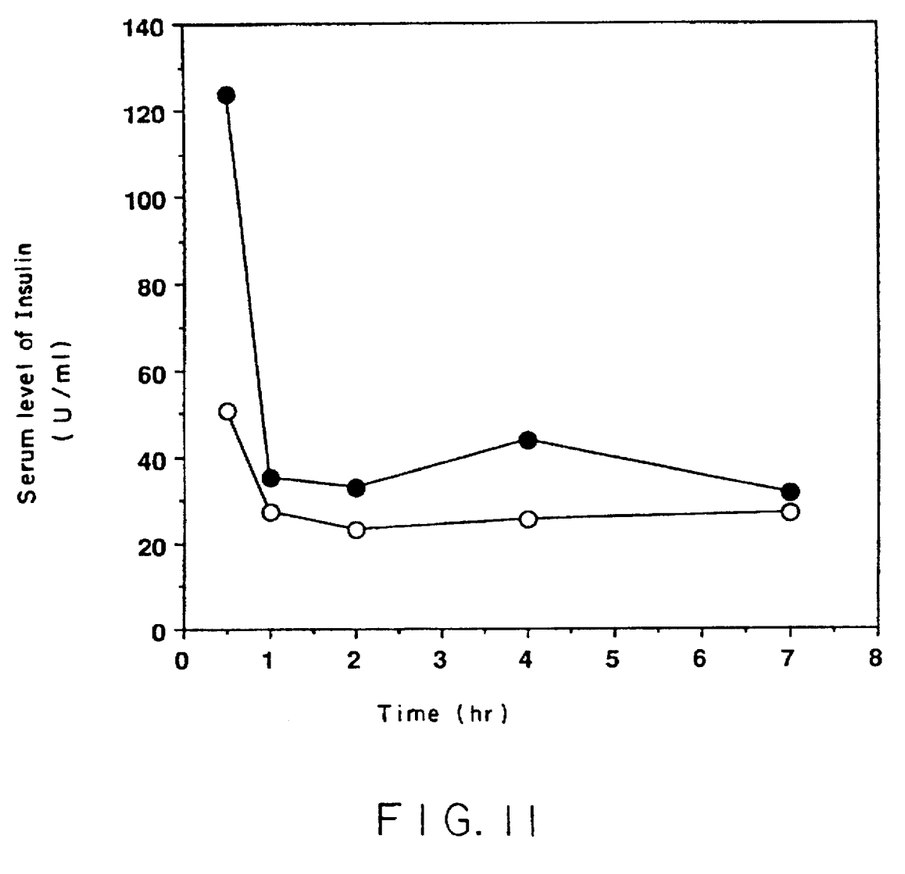
FIG. 11 shows the time course of serum concentration of insulin.

Male SD rats (8 weeks old) were subjected to light anesthesia with diethyl ether and 5 μl of the preparation of Example 15 or Comparative Preparation 9 was administered directly into one nostril. For administration, the exclusive micropipet tip (Excelmidigi 8000, D-5, Sanko Junyaku) was inserted far enough into the nostril. After recovery from anesthesia (in just less than about 15 minutes), the rats were returned to feeding cages and allowed food and water ad libitum. The blood was serially collected from the tail vein and the serum concentration of human insulin was determined. The time course of serum concentration of human insulin is shown in (FIG. 11).

In the group (○) given Comparative Preparation 9, the serum concentration reached a high level immediately after administration and, then, declined. In the group given the citicolin-containing preparation of Example 15 (●), the serum concentration similarly reached a high level immediately following administration and then declined. However, throughout the entire observation period, the serum level was consistently higher in this group as compared with the group given Comparative Preparation 9, indicating that the inclusion of citicoline promotes the absorption of insulin.

---

What is claimed is:

1. A transmucosal therapeutic composition comprising a physiologically active peptide or protein and an absorption promoting amount of cytidine diphosphate choline.

2. A composition according to claim 1, wherein the physiologically active peptide or protein is an antibiotic, a hematopoietic, an antiinfective agent, an antidementia agent, an antiviral agent, an antitumoral agent, an antipyretic, an analgesic, an antiinflammatory agent, an antiulcer agent, an antiallergic agent, an antidepressant, a psychotropic agent, a cardiotonic, an antiarrythmic agent, a vasodilator, an antihypertensive agent, an antidiabetic agent, an anticoagulant, a cholesterol lowering agent, a therapeutic agent for osteoporosis, a hormone or a vaccine.

3. A method for preventing or treating osteoporosis which comprises administering the composition according to claim 2 to a postmenopausal woman through a mucosal membrane, wherein the physiologically active peptide or protein is a therapeutic agent for osteoporosis.

4. A composition according to claim 1, wherein the weight ratio of the physiologically active peptide or protein to the cytidine diphosphate choline is 10,000:1 through 1:10,000 (w/w).

5. A composition according to claim 1, wherein the composition is a liquid dosage form which contains a cytidine diphosphate choline in a concentration of 0.01 to 24% (w/v) in water.

6. A composition according to claim 1, wherein the physiologically active peptide or protein is a cytokine, a peptide hormone, a growth factor, a factor acting on the cardiovascular system, a factor acting on the central and peripheral nervous systems, a factor acting on humoral electrolytes and hemal organic substances, a factor acting on bone and skeleton, a factor acting on the gastrointestinal system, a factor acting on the immune system, a factor acting on the respiratory system, a factor acting on the genital organs or an enzyme.

7. A composition according to claim 6, wherein the cytokine is a lymphokine selected from the group consisting of interferons and interleukins.

8. A composition according to claim 7, wherein the cytokine is interferon α.

9. A composition according to claim 6, wherein the peptide hormone is parathyroid hormone or a parathyroid hormone active fragment thereof, insulin, growth hormone, luteinizing hormone releasing hormone, adrenocorticotropic hormone, oxytocin or luteinizing hormone.

10. A composition according to claim 9, wherein the peptide hormone is insulin.

11. A composition according to claim 6, wherein the factor acting on bone and skeleton is parathyroid hormone or a parathyroid hormone active fragment thereof.

12. A composition according to claim 11, wherein said parathyroid hormone active fragment is a peptide having an amino acid sequence designated by Sequence ID No. 1 or No. 2.

13. A composition according to claim 11, wherein parathyroid hormone active fragment is a peptide having an amino acid sequence consisting of the 34 amino acids of parathyroid hormone, starting from the N-terminus.

14. A transmucosal therapeutic composition comprising a physiologically active peptide or protein and a cytidine diphosphate choline, wherein the composition is a liquid dosage form which contains a cytidine diphosphate choline in a concentration of 0.01 to 24% (w/v) in water and is administered through nasal or vaginal mucosa.

* * * * *